United States Patent [19]

Lew

[11] Patent Number: 5,364,634

[45] Date of Patent: Nov. 15, 1994

[54] CONTROLLED-RELEASE PH SENSITIVE CAPSULE AND ADHESIVE SYSTEM AND METHOD

[75] Inventor: Chel W. Lew, San Antonio, Tex.

[73] Assignee: Southwest Research Institute, San Antonio, Tex.

[21] Appl. No.: 790,639

[22] Filed: Nov. 8, 1991

[51] Int. Cl.⁵ .............................................. A61K 9/48
[52] U.S. Cl. .................... 424/451; 424/434; 424/435; 424/452; 424/457; 424/460
[58] Field of Search ............... 424/435, 451, 496, 434, 424/471

[56] References Cited

U.S. PATENT DOCUMENTS

| | | | |
|---|---|---|---|
| Re. 33,093 | 10/1989 | Schiraldi et al. | 424/676 |
| 3,184,386 | 5/1965 | Stephenson | 424/471 |
| 3,441,507 | 4/1969 | Schiefer et al. | 252/95 |
| 3,598,122 | 4/1969 | Zaffaroni | 128/268 |
| 3,598,123 | 4/1969 | Zaffaroni | 128/268 |
| 3,896,033 | 7/1975 | Grimm | 252/8.8 |
| 3,904,444 | 9/1975 | Anderson et al. | 148/526 |
| 3,911,099 | 10/1975 | DeFoney | 424/435 |
| 3,959,540 | 5/1976 | Leiberich et al. | 428/35.7 |
| 4,124,521 | 11/1978 | Jedzinak | 252/127 |
| 4,144,317 | 3/1979 | Higuchi et al. | 424/21 |
| 4,205,060 | 5/1980 | Monsimer et al. | 424/495 |
| 4,292,299 | 9/1981 | Suzuki et al. | 424/435 |
| 4,416,791 | 11/1983 | Haq | 252/90 |
| 4,657,784 | 4/1987 | Olson | 427/213 |
| 4,685,883 | 8/1987 | Jernberg | 433/215 |
| 4,780,320 | 10/1988 | Baker | 424/497 |
| 4,876,092 | 10/1989 | Mizobuchi et al. | 424/435 |
| 4,889,720 | 12/1989 | Konishi | 424/448 |
| 4,892,736 | 1/1990 | Goodson | 424/443 |
| 4,900,552 | 2/1990 | Sanvordeker et al. | 424/422 |
| 4,915,948 | 4/1990 | Gallopo et al. | 424/435 |
| 4,940,587 | 7/1990 | Jenkins et al. | 424/480 |
| 4,983,392 | 1/1991 | Robinson | 424/427 |
| 5,051,263 | 9/1991 | Barry | 424/451 |
| 5,064,650 | 11/1991 | Lew | 424/451 |

FOREIGN PATENT DOCUMENTS

| | | |
|---|---|---|
| 968248 | 5/1975 | Canada . |
| 0101418 | 2/1984 | European Pat. Off. . |
| 0205282 | 12/1986 | European Pat. Off. . |
| 2132216 | 3/1972 | France . |
| 100714 | 8/1981 | Japan . |
| 0116631 | 6/1985 | Japan . |
| 931149 | 7/1963 | United Kingdom . |
| 1390503 | 4/1975 | United Kingdom . |

OTHER PUBLICATIONS

Smart, et al., "An In-vitro investigation of mucosa-adhesive materials for use in controlled drug delivery", 36 *J. Pharm. Pharmacol.* 295–299 (1984).

Park, et al., "Bioadhesive polymers as platforms for oral-controlled drug delivery: method to study bioadhesion", 19 *Intl. J. Pharm.* 107–127 (1984).

Peppas, et al., "Surface, interfacial and molecular aspects of polymer bioadhesion on soft tissues", 2 *J. Controlled Release* 257–275 (1985).

Longer, et al., "Bioadhesive polymers as platforms for oral controlled drug delivery III: oral delivery of chlorothiazide using a bioadhesive polymer", 74 (4) *J. Pharm. Sci.* 406–411 (Apr. 1985).

Ch'ng, et al., "Bioadhesive polymers as platforms for oral controlled drug delivery II: synthesis and evaluation of some swelling, water-insoluble bioadhesive polymers", 74 (4) *J. Pharm. Sci.* 399–405 (Apr. 1985).

*Primary Examiner*—Gabrielle Phelan

[57] ABSTRACT

A capsule and method for delivery for an active ingredient in the oral cavity that has a pH sensitive encapsulant shell and is associated with an adhesive. The pH sensitive shell dissolves at a pH in the oral cavity while the adhesive allows dissolution at the selected tissue.

24 Claims, No Drawings

CONTROLLED-RELEASE PH SENSITIVE CAPSULE AND ADHESIVE SYSTEM AND METHOD

BACKGROUND OF THE INVENTION

Encapsulation processes have been developed to make capsules containing a selected ingredient or mixtures of ingredients coated with a layer of another composition. Capsules can be made in many sizes. Small capsules come in various size ranges from about 1 micron to several millimeters. The smallest capsules can be used in emulsion formulas. The smaller capsules are sometimes referred to as microcapsules.

Some microcapsules are designed to break under pressure so that the internal ingredient is released when rubbed over a surface. Microcapsules have been made containing therapeutic agents to be ingested coated with films broken down because of pH changes in the gastric system. Other films or shells on capsules are soluble in particular solvents. Release of the internal component is controlled generally by solubility characteristics and the thickness of the shell.

The microcapsules are made by methods well known in the art and have been used in numerous industrial and commercial applications. Typical processes are centrifugal extrusion, pan coating and air suspension methods. U.S. Pat. Nos. 3,692,690; 3,015,128 and 3,310,612 are exemplary of encapsulation techniques known and practiced in the art. In addition to those illustrated by the patents, other techniques are available. The present invention can utilize any of the available methods for preparing capsules or microcapsules.

SUMMARY OF THE INVENTION

The invention is a capsule for oral use containing at least one active ingredient which is coated with a shell of a non-toxic pH sensitive material. The pH sensitive capsules are associated with a non-toxic adhesion system. In this invention pH sensitivity relates to the stability of the shell of the capsule or microcapsule in varying pH ranges. The pH sensitive encapsulation material is a stable shell surrounding the active ingredients when the pH is maintained at a preselected level. Increasing the pH above the preselected level causes the pH sensitive shell to lose its structure, break down, dissolve and release the active ingredient(s) into the oral cavity at the adhesion site. A number of polymers, such as Eudragit® E, L, and S (arylic resins manufactured by Rohm GMBH); hydroxypropyl methylcellulose phthalate; hydroxypropyl methylcellulose acetate succinate; polyvinyl acetate phthalate; cellulose acetate phthalate; and cellulose acetate trimellitate are stable at certain preselected pH and are unstable or dissolve at a higher pH level. Also, plasticized hydrocarbon gel made of a mixture of polyethylene and mineral oil can be used.

The adhesive system associated with the pH sensitive encapsulated active ingredient does not affect the stability of the capsule shell. The adhesive is associated with the outer shell and may be combined to form a pH sensitive bioadhesive encapsulant. The adhesive system permits adhesion of the capsule to selected tissue inside the mouth for a sustained period of time to allow for dissolution. The adhesive system may be in an aqueous gel with the pH of the gel adjusted to a preselected range to maintain the stability of the capsule shell.

The capsules are formulated so that when they are placed in the human mouth with the normal pH level, the capsules destabilize or dissolve and release the active ingredient. The shell's composition can be formulated to provide slow or fast rate of dissolution. The capsules used with the adhesive system provide a mixture which can be placed inside the mouth on selected tissue. The capsules dissolve over a sustained period of time while the adhesion system holds them in place. The active ingredient or mixture of ingredients is released over time in a specific region of the oral cavity.

The characteristics and release of the active ingredient are a consideration in designing the capsule of this invention. A water soluble active ingredient is best not encapsulated with a water soluble pH sensitive shell. If the active ingredient is water soluble, a water insoluble film layer, such as a lipid, may enclose the active ingredient which in turn is coated with the pH sensitive shell. There would be a two layer process for encapsulation so that the internal soluble ingredient will be protected from the pH sensitive shell with the water insoluble layer. The water insoluble layer is water dispersible so that the active ingredient is released once the capsule is placed in a pH to destabilize the pH sensitive layer exposing the lipid layer. A lipid layer may also be desirable for changing the release characteristics of the active ingredient.

The active ingredient can be any drug, therapeutic compound or oral treatment desired to be released in the oral cavity such as drugs, antibiotics, enzymes, anesthetics, breath fresheners, flavors, preservatives or mixtures thereof. Some drugs are subject to enzymatic attack in the gastric system, and delivery through the oral cavity is preferred in order to maintain the active form of the compound.

Microcapsules can be formulated with previously described active ingredients and encapsulation compositions to produce one or two layer shells around the active ingredient(s). The microcapsules are placed in the adhesive system to produce a matrix of microcapsules that can adhere to a site selected in the oral cavity. The pH sensitive outer shell will break down and dissolve releasing the contents of the microcapsule. The composition and the thickness of the shell can be adjusted to control the release rate of the active ingredient(s). The matrix may contain a mixture of microcapsules encapsulating different active ingredients as desired.

DETAILED DESCRIPTION OF THE INVENTION

The following description of the invention is for particular embodiments of capsules including microcapsules that can be used for oral treatment and medication. The invention is for a non-toxic, pH sensitive shell for release of an active ingredient such as medication or a breath freshener for use in the oral cavity. The active ingredient is contained inside the pH sensitive shell and is not released until the shell destabilizes or dissolves in the mouth. The capsules are associated with a nontoxic adhesive system in which the bioadhesive is associated with the outer shell of the capsules or the bioadhesive is a gel coating or matrix containing the capsules. The adhesive system is compatible with the pH sensitive shell such that the stability of the shell is not affected by the adhesive.

A pH sensitive shell can be used to encapsulate one or more active ingredients. Also, a mixture of microcapsules encapsulating different active ingredients may be used. Certain active ingredients may be reactive with the compound or compounds selected for the pH sensitive shell. Also, there may be a need to vary the release characteristics of the active ingredient. In addition, some active ingredients may be soluble with the pH sensitive shell. In these cases, a non-toxic water dispersible lipid coating can be used to encapsulate the internal component which in turn is coated with an outer shell of pH sensitive compound. The capsule has a two layer coating. The lipid coating is water dispersible so that the active ingredient will be released in the oral cavity. The internal component of the capsule will be released upon the dissolution of the pH sensitive outer layer in a diluted salt concentration level and the subsequent dispersal of the lipid layer.

The capsules can be made as microcapsules using known encapsulation techniques such as centrifugal extrusion, pan coating and air suspension. The capsules of this invention include microcapsules and the broad categories of known capsules and encapsulation techniques. The pH sensitive encapsulation material is capable of forming a stable shell at a pH less than the pH of the oral cavity. The typical range in the oral cavity is pH 6.4 to pH 7. The capsules or microcapsules for use in the oral cavity should be maintained at a pH of less than 6. The adhesive system is formulated or adjusted to maintain a pH range at a level to stabilize the encapsulating material. If there will be a variance from the pH range in the oral cavity for any reason, the pH sensitive material can be selected based on the different pH criteria needed for the dissolution of the capsules. The shell compound for encapsulation, therefore, will be selected for the pH environment in which dissolution is desired and stored in a pH preselected to maintain the shell stability.

Examples of pH sensitive material useful as encapsulants are Eudragit ® L-100 or S-100 (arylic resins manufactured by Rohm GMBH), hydroxypropyl methylcellulose phthalate, hydroxypropyl methylcellulose acetate succinate, polyvinyl acetate phthalate, cellulose acetate phthalate, and cellulose acetate trimellitate.

Lipids are preferred as the inner coating. Examples are food grade Span ® which are partial esters of fatty acids and hexitiol anhydrides. Also, edible fats such as triglycerides are suitable.

Many types of active ingredients can be encapsulated for delivery in the oral cavity. Antibiotics suitable for oral delivery are vancomycin, gentamicin, imipenem, penicillin and ceptazidime. Other active ingredients can be anesthetics, such as ethyl aminobenzoate (benzocaine); antifungals such as ketoconazole; or an anthelmintic such as mebendazole (Vermox ®).

The capsules may be maintained and applied in an aqueous gel adhesive system which has a pH of a preselected range to maintain the integrity of the outer shell of the capsule. More than one active ingredient may be included inside the shell as long as the active ingredient or mixture does not adversely affect the stability of the shell. For instance, a water insoluble flavoring oil may be mixed with the benzocaine for an oral anesthetic. It may be desirable to include a preservative.

Examples of bioadhesives that can be associated with a capsule or as a coating or in a gel adhesive system are calcium polycarbophil, polyacrylic acid, gelatin, carboxymethyl cellulose, natural gums such as karaya and tragacanth, algin, chitosan, hydroxypropylmethyl cellulose, starches, pectins or mixtures thereof. The adhesives can be coated on the capsule shell or made part of the capsule shell provided there is compatibility with the shell composition to maintain integrity.

The adhesives may be mixed with a hydrocarbon gel base, composed of polyethylene and mineral oil, with a preselected pH level to maintain the capsule stability.

The adhesive gel is adjusted to a preselected pH. The capsules are dispersed in the gel. The gel containing the capsules is applied to the tissue in the oral cavity where the delivery of the active ingredient is desired.

The following are examples of a capsule or microcapsule delivery system for benzocaine, a local anesthetic. The adhesive is mixed with the outer shell component to produce a bioadhesive gel outer shell.

EXAMPLE 1

| Component | % by Weight |
|---|---|
| Outer Shell | |
| Plasticized hydrocarbon gel of 60% polyethylene and 40% mineral oil | 75.0 |
| Adhesive (mixed with outer shell) | |
| Guar gum | 1.5 |
| Carboxymethyl cellulose | 1.5 |
| Gum tragacanth | 0.9 |
| Pectin | 0.5 |
| Active Ingredients | |
| Benzocaine | 20.0 |
| Flavor | 0.5 |
| Preservative | 0.1 |

EXAMPLE 2

| Component | % by Weight |
|---|---|
| Outer Shell and Adhesive | |
| Gel base of pectin, gelatin, carboxymethylcellulose and water | 72.4 |
| Polyethylene glycol | 1.0 |
| Active Ingredients | |
| Benzocaine | 20.0 |
| Oil (e.g. clove) | 5.0 |
| Flavor oil | 1.0 |
| Sodium saccharin | 0.5 |
| Sorbic acid | 0.1 |

The adhesives of this invention allow the capsules or microcapsules to be placed in the mouth and adhere to the tissue in the oral cavity for a sustained period of time for delivery of the drug, antibiotics, local anesthetic, breath freshener or other active ingredients. The description and examples will enable those skilled in the art to formulate alternative embodiments of the invention.

I claim:

1. A capsule for adhesion in the oral cavity comprising
   at least one internal active ingredient;
   a non-toxic pH sensitive shell encapsulating said active ingredient and said shell is insoluble in a preselected pH of less than 6;
   said shell dissolving at the pH 6.4 and above which is present in the oral cavity; and
   a non-toxic adhesive system associated with the outer surface of said shell which permits adhesion of the capsule to selected tissue inside the oral cavity for a period of time to allow for the dissolution of said shell and release of the active ingredient.

2. A capsule for adhesion in the oral cavity of claim 1 additionally comprising a water dispersible lipid coating surrounding the active ingredient which is encapsulated with the pH sensitive shell.

3. A capsule for adhesion in the oral cavity of claim 1 wherein said active ingredient is selected from the group consisting of drugs, enzymes, breath fresheners, flavors, preservatives, or mixture thereof.

4. A capsule for adhesion in the oral cavity of claim 1 wherein said pH sensitive shell is selected from the group of pH sensitive acrylic resins, plasticized hydrocarbon gel, hydroxypropyl methylcellulose phthalate, hydroxypropyl methylcellulose acetate succinate, polyvinyl acetate phthalate, cellulose acetate phthalate, cellulose acetate trimellitate, and mixtures thereof.

5. A capsule for adhesion in the oral cavity of claim 1 wherein said adhesive system is selected from the group of calcium polycarbophil, polyacrylic acid, gelatin, carboxymethyl cellulose, natural gums, algin, chitosan, hydroxypropylmethyl cellulose, starches, pectins or mixtures thereof which are applied to the outside of the shell of the capsules.

6. A capsule of claim 1 wherein the non-toxic pH sensitive shell and the adhesive are combined to form a pH sensitive bioadhesive encapsulant.

7. A formulation for adhesion in the oral cavity comprising
a plurality of capsules made of at least one internal active ingredient with a non-toxic shell encapsulating said active ingredient which is insoluble at a preselected pH of less than 6 and said non-toxic shell dissolving at the pH 6.4 and above which is present in the oral cavity; and
said capsules contained in a non-toxic adhesive system such that the mixture of the capsules and the adhesive allows for the adhesion of the mixture to a selected site inside the oral cavity for a sustained period of time to allow for the dissolution of the shell and the release of the active ingredient.

8. A formulation for adhesion in the oral cavity of claim 7 wherein said non-toxic adhesive system comprises an aqueous gel with a pH at a preselected level to maintain the integrity of the pH sensitive shell of the capsules.

9. A method of delivering an active ingredient to the oral cavity comprising the steps of
encapsulating at least "one" active ingredient with a non-toxic shell which is insoluble at a preselected pH of less than 6 to form microcapsules;
associating a plurality of microcapsules with an adhesive system which does not affect the stability of the shell;
maintaining the stability of the microcapsules by keeping the microcapsules at a pH at which the shell is insoluble and stable; and
introducing the microcapsules with the adhesive system associated therewith into the oral cavity, the adhesive system causing the microcapsules to adhere to a selected site in the oral cavity for a period of time, the pH 6.4 and above which is present in the oral cavity destabilizing the shell of the microcapsules thereby releasing the active ingredient at the selected site in the oral cavity.

10. A method of claim 9 additionally comprising the step of encapsulating the active ingredient with an inner lipid coating which is dispersible inside the oral cavity before encapsulating with the pH sensitive material.

11. A method of claim 9 wherein said encapsulant and said adhesive are combined to form a pH sensitive bioadhesive encapsulant.

12. A method of claim 9 wherein the adhesive forms a matrix containing the capsules.

13. A method of claim 9 wherein said active ingredient is selected from the group consisting of drugs, enzymes, breath fresheners, flavors, preservatives, or mixture thereof.

14. A method of claim 9 wherein said pH sensitive shell is selected from the group of pH sensitive acrylic resins, plasticized hydrocarbon gel, hydroxypropyl methylcellulose phthalate, hydroxypropyl methylcellulose acetate succinate, polyvinyl acetate phthalate, cellulose acetate phthalate, cellulose acetate trimellitate, and mixtures thereof.

15. A method of claim 9 wherein said adhesive system is selected from the group of calcium polycarbophil, polyacrylic acid, gelatin, carboxymethyl cellulose, natural gums, algin, chitosan, hydroxypropylmethyl cellulose, starches, pectins and mixtures thereof which are applied to the outside of the shell of the capsules.

16. A delivery system for adhesion to the oral cavity comprising
a plurality of microcapsules with at least one active ingredient surrounded by an outer shell that is stable at preselected pH of less than 6 and dissolves in the oral cavity at a pH of 6.4 and above which is present in the oral cavity;
an adhesive associated with the outer shell of the microcapsule which does not affect the integrity of the outer shell; and
said adhesive causing adhesion of the microcapsules in the oral cavity for a period of time to allow dissolution of the shell and release of the active ingredient.

17. A delivery system for the oral cavity of claim 16 additionally comprising a water dispersible inner lipid layer surrounding the active ingredient between the outer shell and said active ingredient.

18. A delivery system of claim 16 wherein the adhesive forms a matrix containing the microcapsules.

19. A delivery system of claim 16 wherein the adhesive is an aqueous gel with the pH adjusted to the preselected level to maintain the integrity of the outer shell of the microcapsules.

20. A delivery system of claim 16 wherein the microcapsules are a mixture of microcapsules encapsulating selected active ingredients.

21. A delivery system of claim 16 wherein said outer shell and adhesive are combined to form a pH sensitive bioadhesive encapsulant.

22. A delivery system of claim 16 wherein said adhesive is selected from the group of calcium polycarbophil, polyacrylic acid, gelatin, carboxymethyl cellulose, natural gums, algin, chitosan, hydroxypropylmethyl cellulose, starches, pectins and mixtures thereof.

23. A delivery system of claim 16 wherein said pH sensitive shell is selected from the group of pH sensitive acrylic resins, plasticized hydrocarbon gel, hydroxypropyl methylcellulose phthalate, hydroxypropyl methylcellulose acetate succinate, polyvinyl acetate phthalate, cellulose acetate phthalate, and cellulose acetate trimellitate.

24. A delivery system of claim 16 wherein said active ingredients are selected from the group of drugs, enzymes, breath fresheners, flavors, preservatives, and mixtures thereof.

* * * * *